United States Patent [19]
Bokros et al.

[11] Patent Number: 6,096,075
[45] Date of Patent: Aug. 1, 2000

[54] PROSTHETIC HEART VALVE

[75] Inventors: Jack C. Bokros; Jonathan C. Stupka; Robert B. More, all of Austin, Tex.

[73] Assignee: Medical Carbon Research Institute, LLC, Austin, Tex.

[21] Appl. No.: 09/010,449

[22] Filed: Jan. 22, 1998

[51] Int. Cl.$^7$ .................................................. A61F 2/24
[52] U.S. Cl. ............................................................ 623/2.33
[58] Field of Search ........................................ 623/2, 900

[56] References Cited

U.S. PATENT DOCUMENTS

| | | |
|---|---|---|
| 4,078,268 | 3/1978 | Possis . |
| 4,276,658 | 7/1981 | Hanson et al. . |
| 4,451,937 | 6/1984 | Klawitter . |
| 4,689,046 | 8/1987 | Bokros . |
| 5,123,920 | 6/1992 | Bokros . |
| 5,152,785 | 10/1992 | Bokros et al. . |
| 5,171,263 | 12/1992 | Boyer et al. . |
| 5,197,980 | 3/1993 | Gorshkov et al. ............................ 623/2 |
| 5,314,467 | 5/1994 | Shu . |
| 5,354,330 | 10/1994 | Hanson et al. . |
| 5,376,111 | 12/1994 | Bokros et al. . |
| 5,641,324 | 6/1997 | Bokros et al. . |
| 5,824,062 | 10/1998 | Patke et al. .................................. 623/2 |

FOREIGN PATENT DOCUMENTS

W09629957  10/1996  WIPO .
WO9705834  2/1997  WIPO .

*Primary Examiner*—David H. Willse
*Attorney, Agent, or Firm*—Fitch, Even, Tabin & Flannery

[57] ABSTRACT

A prosthetic heart valve comprising a tubular valve body and a pair of leaflets which pivot, or translate and pivot, between open and closed positions. The valve body is of circular interior cross-section except for a pair of diametrically opposed flat wall sections which contain recesses within which the pivot axes of the leaflets are located. Arcuate edges of the leaflets are irregularly shaped so that a pair of protrusions extend radially outward from an otherwise generally semicircular periphery. The protrusions are strategically located so as to contact the interior surface of the valve body in the closed position at arcuately spaced apart locations which flank the centerline of the leaflet. As a result, contact in the closed position occurs at two spaced apart locations rather than at a single location, and at least a minimum gap is established at the central tip of the leaflet which counteracts potential cavitation, noise and hemolysis.

18 Claims, 4 Drawing Sheets

PROSTHETIC HEART VALVE

FIELD OF THE INVENTION

The present invention relates to mechanical heart valve prostheses and to improvements which are particularly but not exclusively useful in bileaflet heart valves which include a pair of valve members or occluders that undergo at least some pivotal movement in reaching their closed orientation.

BACKGROUND OF THE INVENTION

A variety of mechanical heart valve prostheses have been developed which operate hemodynamically, in conjunction with the pumping action of the heart, to take the place of a defective natural valve. These valves include constructions having valve members in the form of a single occluder, a pair of occluders or three or more occluders; however, to date, heart valves of the bileaflet type have generally been the preferred mechanical heart valves.

U.S. Pat. No. 4,276,658 to Hanson et al. discloses a bileaflet heart valve made of pyrocarbon-coated graphite which has been sold in the United States for over a decade.

U.S. Pat. No. 4,689,046 to Bokros shows another similar bileaflet heart valve design wherein a pair of flat leaflets have straight mating edges which mate with each other at the center of the valve and have arcuate edges that seat against the interior circular cylindrical wall of the valve body.

U.S. Pat. No. 4,451,937 to Klawitter discloses heart valves wherein flat occluders and occluders of complex curvature are guided by ears that travel in arcuate recesses and pivot upon pairs of upper and lower protuberances which end radially inward from the wall of the valve body. In the closed positions in some of the valves, a pair of leaflets are oriented generally perpendicular to the centerline of the valve body and the tips of the leaflets abut midpoint stops that extend inward from the valve body interior wall. Similar single occluder valve constructions are also shown.

U.S. Pat. No. 5,123,920 to Bokros shows a bileaflet heart valve having leaflets that are aerodynamically shaped and that have rectilinear surfaces which are curved in a direction parallel to the pivot axes.

U.S. Pat. No. 5,152,785 to Bokros et al. shows a bileaflet heart valve having leaflets that are flat and leaflets that are curved in a direction generally parallel to the centerline axis through the valve when the leaflets are in the open position.

U.S. Pat. No. 5,171,263 to Boyer et al. shows a bileaflet heart valve having leaflets that are curved in a direction parallel to the pivot axes and which contact an abutment extending radially inward from the valve body interior wall to define the closed position.

U.S. Pat. No. 5,314,467 to Shu shows a bileaflet heart valve having leaflets of complex curvature.

U.S. Pat. No. 5,354,330 to Hanson et al. shows a bileaflet heart valve of this general type having flat leaflets which rotate on spherical pivots and have circular edges which seat against the interior surface of the valve body.

U.S. Pat. No. 5,376,111 to Bokros et al. shows bileaflet and single occluder valves where the occluders may be flat or curved.

U.S. Pat. No. 5,641,324 to Bokros et al. shows an improved bileaflet heart valve of this general type having a novel valve body entrance and a novel pivot mechanism. The disclosures of all these U.S. patents are incorporated herein by reference.

The more that such mechanical prosthetic valves have been studied, the more that investigators have concluded that the ideal prosthetic valve simply does not yet exist. From a materials standpoint, pyrolytic carbon has been determined to be adequately nonthrombogenic; as a result, the problem of combatting thrombosis in mechanical valves is presently felt to lie in preventing excess turbulence, high shear stresses, cavitation and local regions of stasis. Blood is a very delicate tissue, and even minor abuses caused by cavitation, turbulence and high shear stress can cause either hemolysis, thrombosis and/or emboli generation at local regions of stagnation. Cavitation in regions near surfaces of the structural components can cause erosion that, if serious, can lead to valve failure. Therefore, it is felt that future improvement in the characteristic of thromboresistance in mechanical valves will likely be attained through the achievement of smooth, nonturbulent flow and the absence of cavitation and stasis.

The search continues for improved mechanical heart valve prostheses that provide passageways through which blood will flow freely and with a minimum of drag in the open position, which will close quickly without cavitation or significant noise upon the occurrence of backflow to minimize regurgitation of blood, and which can be efficiently manufactured and assembled. Accordingly, new valve designs incorporating such features have continued to be sought.

SUMMARY OF THE INVENTION

The present invention provides mechanical bileaflet heart valve prostheses having the aforementioned desirable characteristics wherein the leaflets are designed to abut interior, generally cylindrical surfaces of the valve body in the closed position in such a manner that cavitation and noise are minimized at the time of contact. Mechanical bileaflet heart valves sold in the United States to date have generally been designed so that the central tip of the arcuate edge of each leaflet will contact the interior wall surface, as a result of which the region of contact between the rectilinear arcuate edge and the rectilinear interior surface of the valve body will be along a line or a short arcuate surface segment located at or adjacent what may be termed the centerline of the leaflet. The remainder of the arcuate edge of the leaflet will lie in juxtaposition with the interior wall, with the extent of the gap depending upon manufacturing tolerances, because there will only be a single location where contact exists.

In the construction of the present invention, the valve body and the leaflets are shaped so that there is contact at two locations flanking the centerline of the leaflet, and so that there is a distinct gap between the central tip of the leaflet and the interior wall surface of the valve body. As a result of this construction, contact between the closing leaflet and the interior wall is shifted from a single point adjacent the centerline location to a pair of locations which are each preferably positioned spaced from the leaflet centerline by about 30° to about 55° of arc, and a minimum gap of preferably at least about 0.002 inch is created at the centerline location.

Because the center tip of the leaflet as it is pivoting to its final closed orientation is moving with the greatest velocity of any point along the arcuate edge, the provision of such a minimum gap at this precise location minimizes cavitation at the instant of closing that would otherwise potentially result in erosion and/or hemolysis. Moreover, by shifting the points of contact and the valve body interior wall to two spaced apart locations a substantial distance further outward along the arcuate edge from the central tip, the tangential velocity at which these two points along the edge are traveling when they make contact is substantially less than the tangential velocity at the center tip. In addition, if one focuses on the leaflet velocity vector directed perpendicular to the valve body wall (which is a primary cause of cavitation), one finds that such vector is a maximum at the leaflet central tip or midpoint and diminishes significantly as one moves away from the midpoint to contact points remote from the midpoint. Therefore, not only is the tangential velocity ($V_c$) reduced as one moves further from the midpoint, but the effective velocity perpendicular to the wall is decreased by a factor equal to cosine $\theta$, where $\theta$ is the angle of offset from the midpoint. Overall, by splitting the force of the impact to two locations and by the combination of both significantly reducing the tangential velocity at the point of impact and reducing the effective velocity perpendicular to the wall, cavitation is minimized and the noise generated at the instant of closing is very substantially reduced.

DETAILED DESCRIPTION OF THE PREFERRED EMBODIMENTS

Figure 1:
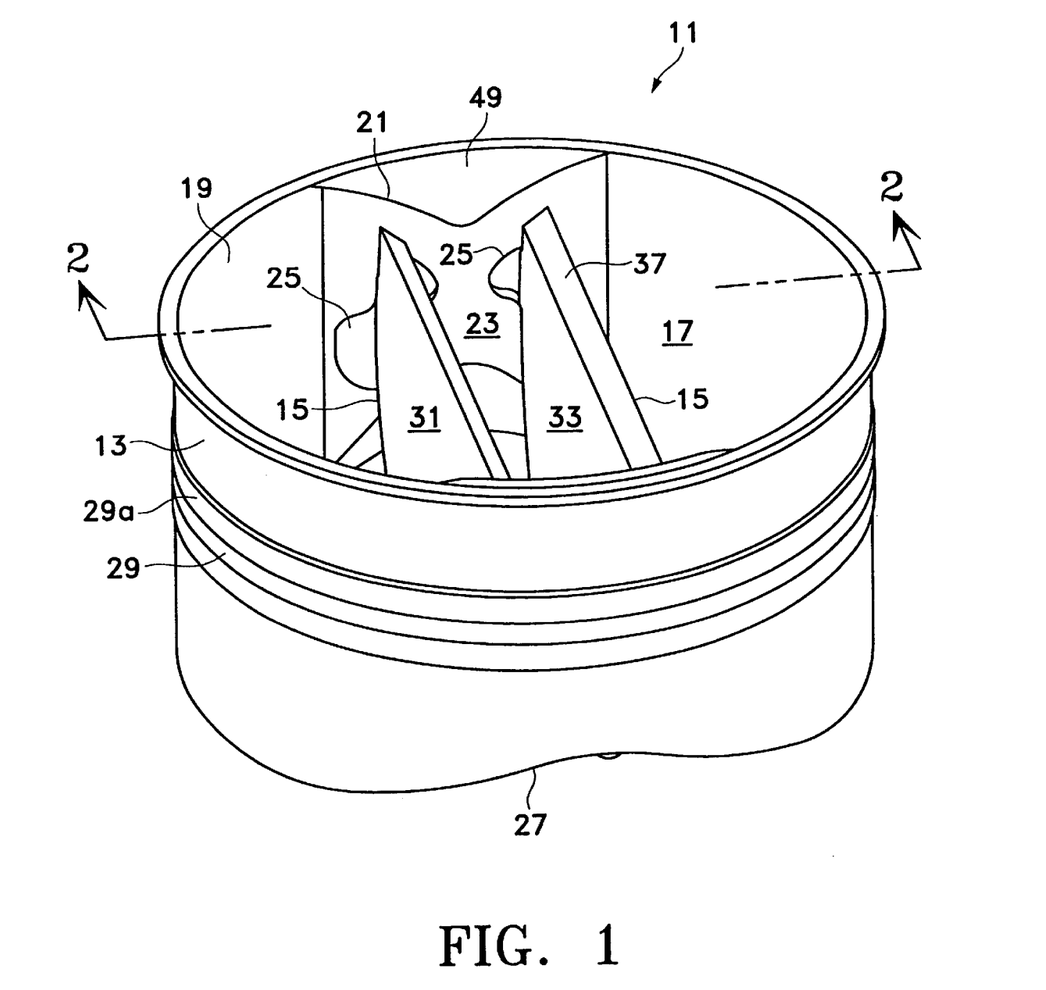
FIG. 1 is a perspective view of a bileaflet heart valve similar to that shown in U.S. Pat. No. 5,641,324 with the leaflets shown in the open position.

Illustrated in FIG. 1 is a prosthetic heart valve 11 constructed so as to embody various features of the present invention. Very generally, the heart valve 11 bears very substantial similarity to the heart valves described and shown in U.S. Pat. No. 5,641,324, the disclosure of which is incorporated herein by reference. The improvement over the design and construction described in detail in the '324 patent is found in the complementary shaping of the arcuate edge of the leaflets and the interior generally cylindrical wall surface of the valve body so that contact between the leaflet edge and the interior wall surface in the closed position occurs at two points, each arcuately spaced from the center tip or midpoint of the leaflet, and so that, at the center tip of the leaflet, there is at least a minimum spacing from the interior wall surface.

Figure 2:
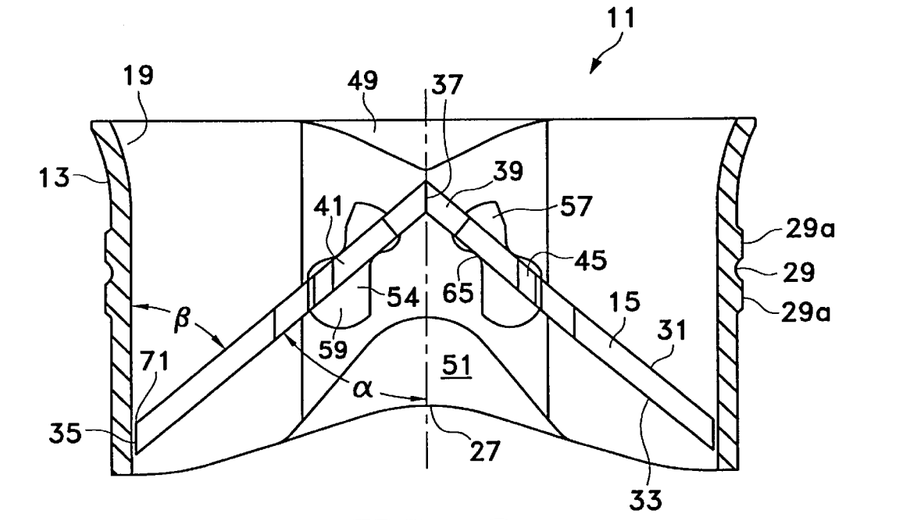
FIG. 2 is a sectional view taken generally along the line 2—2 of FIG. 1 with the leaflets shown in elevation and in their closed position.
Figure 6:
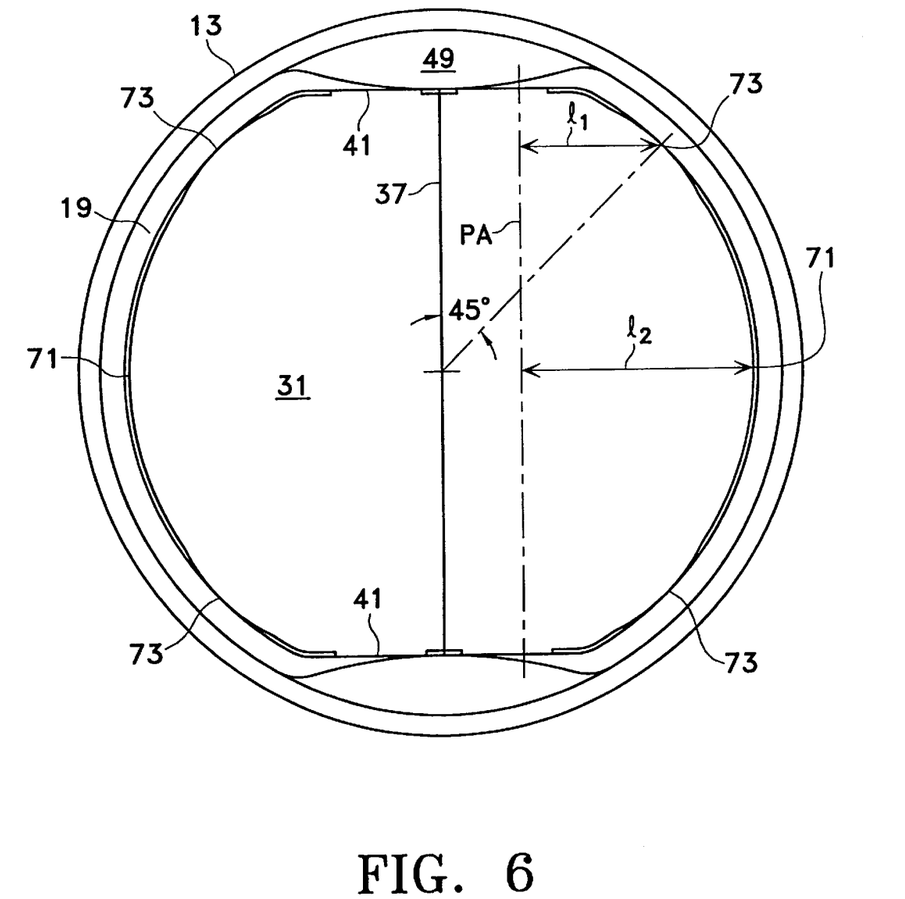
FIG. 6 is a plan view looking downward into the heart valve of FIG. 1 with the leaflets in the closed position.

Heart valve 11 includes a generally annular valve body 13 which carries a pair of pivoting occluders or leaflets 15 that alternately open and close either to allow the smooth flow of blood in the downstream direction, which is vertically downward as depicted in FIG. 1 and FIG. 2, or to prevent any substantial backflow of blood, i.e. regurgitation. The valve body 13 defines a blood flow passageway in the form of its generally arcuate, mostly cylindrical interior wall surface 17. The valve body 13 has a curved entrance region 19 at its upstream end, which has been found to substantially increase streamlined flow characteristics through the valve with low turbulence and substantially no generation of thrombosis. The details of the curved entrance region 19 which extends axially for a distance not greater than about one-third of the average axial length of the valve body are briefly discussed hereinafter along with the operation of the valve. A pair of diametrically opposed, thickened wall sections 21, as best seen in FIG. 6, protrude inward from an otherwise right circular cylindrical surface, terminating in facing, parallel flat wall surfaces 23 in which pairs of cavities or recesses 25 are formed that function as one-half of the pivot arrangement which controls the opening and closing movements of the leaflets 15. Thus, the interior surface downstream of the curved entrance region 19 is generally rectilinear.

The valve body 13 preferably has a scalloped downstream profile so that there are, in effect, a pair of shallow notches 27 formed in the contour of the valve body 13 in the regions just downstream of the thickened wall sections 21. In a bileaflet valve of this type, the side openings provided by these notches 27 are aligned with the central passageway between the leaflets 15 so that, upon reversal of blood flow, backflowing blood laterally enters the valve body through these side openings directing a surge of blood flow into the central passageway region and creating forces which impinge upon the leaflet outflow surfaces, the effect of which is to further enhance prompt pivoting of the eccentrically mounted leaflet toward their closed position orientations. This function is described in greater detail in U.S. Pat. No. 5,308,361, the disclosure of which is incorporated herein by reference.

The exterior surface of the relatively thin valve body 13 in the region downstream of the flared entrance section 19 is substantially that of a surface of a right circular cylinder except for a slightly thickened central portion wherein a shallow groove 29 is formed between a pair of raised bands 29a. An optional metal stiffening ring (not shown) may be mated therewith to add stability and rigidity to the valve body. The valve body itself is preferably made of a suitable material, such as pyrocarbon or pyrocarbon-coated graphite, as is well known in this art, which has sufficient resiliency that it can be deformed so as to permit the insertion of the pair of leaflets 15 in their operative locations. If the pyrocarbon has sufficient rigidity, such a stiffening ring may be unnecessary. Such a metal ring may also be used to assist in supporting a sewing ring of appropriate design, as broadly known in this art. Detailed examples of sewing or suture rings which can be employed are described in U.S. Pat. Nos. 4,535,483 and 5,178,633, the disclosures of which are incorporated herein by reference.

The thickened exterior bands 29a are strategically located in the downstream cylindrical section of the valve body spaced from the flared entrance section 19. The groove 29, which is of arcuate cross section and constitutes the narrowest diameter on the exterior surface, is located so that it is completely downstream of the fulcrums which are formed in recesses 25. This arrangement permits the suture rings to be accommodated in a location where the remaining tissue annulus will be in contact with a portion of the right circular cylindrical exterior surface of the valve body.

The leaflets 15 are preferably identical in shape and size. Each leaflet has two rectilinear, preferably flat, surfaces, i.e. an inflow surface 31 and an outflow surface 33, and each leaflet is preferably of substantially constant thickness such that the surfaces 31 and 33 are parallel to each other. The inflow surface 31 is arbitrarily defined as the surface which faces upstream with the leaflets in the closed position (see FIG. 2), whereas the outflow surface 33 faces downstream. Although the leaflets 15 are preferably flat, other configurations, such as sections of hollow cylinders of circular or elliptical cross section, can alternatively be employed, as discussed in more detail in U.S. Pat. No. 5,246,453, the disclosure of which is incorporated herein by reference.

Each leaflet 15 has a major arcuate edge surface 35, which is located at the downstream edge of the leaflet in the open position, and each has a minor straight mating edge surface 37 which is located at the opposite, upstream edge of the leaflet in the open position. The arcuate edge surface 35 preferably has an irregular contour such as to abut against the cylindrical sidewall interior surface 17 of the valve body at two spaced-apart locations in the closed position, as explained in detail hereinafter. The minor edge surface 37 is preferably flat and formed at an angle to the inflow surface so as to mate flush against the corresponding mating edge surface 37 of the opposing leaflet in the closed position, as best seen in FIG. 2. As a result, the minor edge surface 37 is accordingly oriented at an angle to the inflow surface 31 which is substantially the same as the downstream angle which the outflow surface 33 forms with the centerline plane in the closed position, and it is preferably an angle between about 45° and about 70°. The centerline plane is defined as a plane which includes the centerline of the passageway and which is parallel to the pivot axes of the leaflets; in the illustrated embodiment, it is perpendicular to the flat wall surfaces 23 of the valve body passageway. The angle in question, which is marked α in FIG. 2, defines the extent of the angular rotation that each leaflet 15 will undergo in moving from the fully open position to the fully closed position. There may be an advantage in having a smaller angle, as opposed to a larger angle, because the leaflets need not rotate as great an angular distance in order to reach the fully closed position; however, the smaller the angle, the greater is the force vector directed perpendicular to the wall of the valve body at the instant of closure. As illustrated in FIG. 2, this angle α is about 50° in the preferred embodiment. The angle which the inflow surface 31 forms with the valve body wall in the closed position is marked β, and β=α, being also 50° in the illustrated embodiment.

Figures 3, 4, 5:
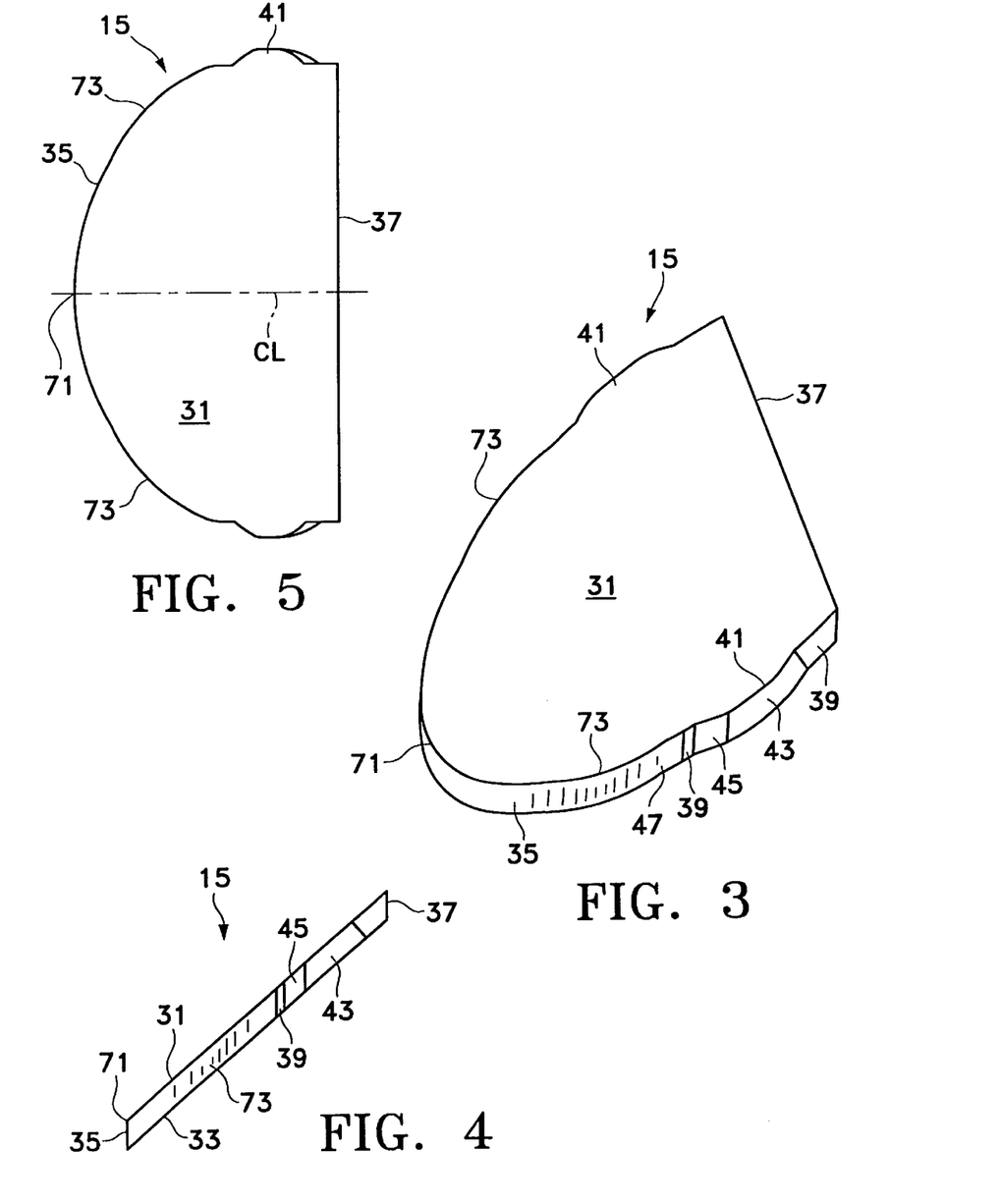
FIG. 3 is a perspective view of a leaflet from the valve shown in FIG. 1.
FIG. 4 is a side elevation view, reduced in size, of the leaflet of FIG. 3.
FIG. 5 is a plan view, reduced in size, of the leaflet of FIG. 3.

As best seen in FIG. 3, the leaflets 15 each have a pair of intermediate straight edge regions 39 located between the minor mating edge surface 37 and the major arcuate edge surface 35 wherein a pair of laterally extending ears or tabs 41 are located. As can be seen in FIG. 4, the ears 41 are the same thickness as the flat leaflets 15 from which they laterally extend. The ears 41 are elongated in an upstream-downstream direction when viewed in their open orientation. FIGS. 3 and 5 show that the ears 41 have lateral edge surfaces which are rectilinear surfaces of generally shallow curvature as viewed looking at the leaflet from the inflow surface 31. More specifically, as best seen in FIG. 3, they each have a shallow rounded upstream edge surface 43 and a generally similar downstream edge surface 45. The upstream edge surface 43 is the longer, extending generally laterally of the ear, and it meets and blends smoothly into the downstream surface 45. The major portion of the rectilinear upstream edge surface 43 is perpendicular to the flat inflow and outflow surfaces of the leaflets 15, which flat surfaces simply extend through the regions of the ears, so that the ears have inflow and outflow surfaces that are coplanar with the leaflet main body inflow and outflow surfaces 31, 33. A short arcuate transition edge section 47 is interposed between the major arcuate edge surface 35 and the flat section 39.

As previously mentioned, the valve body 13 is formed with the thickened wall sections 21 in the regions where the cavities 25 are located, and preferably these thickened sections are formed with flaring transition surfaces, i.e. an upstream transition surface 49 and a downstream transition surface 51 which lead smoothly from the circular entrance region and the circular exit region of the valve body to the flat wall surfaces 23 wherein the cavities 25 are located. A surface such as the surface 49 may be referred to as a radial swept surface. As a result, the flow passageway through the valve body is generally circular in cross-section except for the two thickened sections 21 which extend inward to the flat wall surfaces 23. As previously indicated, the plane containing the centerline axis of the generally circular passageway that is oriented perpendicular to the flat surfaces 23 is referred to as the centerline plane and is sometimes used for reference purposes.

The arrangement is such that each thickened section includes two side-by-side cavities which are mirror images of each other and which are located on opposite sides of this centerline plane. The cavities 25 each have a central flat rear section 54; however, the depth of the cavities 25 is such that the apex of the curved upstream edge surface 43 of the ear does not quite touch the rear walls 54 of the cavities, e.g. a clearance of about 1–4 mils (0.001–0.004 inch). The flat wall surfaces 23 of the thickened regions serve as the primary bearing surfaces against which one or the other of the straight edge surfaces 39 of the leaflets will usually bear whenever the leaflet is moving between its open and the closed positions. The cavities have upstream lobes 57 and downstream lobes 59 which are separated by fulcrums 65. The clearance between the shallow curved edge surface 43 of the ear and the rear wall of the cavity is such to facilitate a controlled cleansing spurt of blood flow, upstream through the cavity past the leaflet ears during the moment of complete closure of the valve as shown in FIG. 2; this arrangement guards against the possibility of the occurrence of clotting in the pivot region. The proportioning of the ears 41 and the cavities is such that this cleansing leak is not a high velocity jet that might cause hemolysis; instead, it is a controlled flow through a long narrow leak path that does not induce thrombosis.

The pivot mechanism of the valve forms no part of the present invention and is described in detail in the aforementioned '324 patent. Very generally, the cavities 25 in the flat sidewall sections 23 of the valve body receive the tabs or ears 41 which extend from the flat lateral edge surfaces 39 of the leaflets and guide the leaflets in their opening and closing movements which are both translational and pivotal. However, the construction and shape of the recesses is such that substantially only rotational motion occurs as the leaflets swing to the fully-closed position.

The leaflets 15 are installed in the valve body 13 by squeezing the body at diametrically opposite locations, as for example along a diameter which is perpendicular to the centerline plane. Such deformation of the heart valve body 13 can take place in accordance with the teachings of U.S. Pat. No. 5,336,259, issued Aug. 9, 1994, the disclosure of which is incorporated herein by reference. Squeezing causes the diametrically opposed flat wall sections 23 to separate farther from each other to permit the leaflets to be fitted into the valve body, with the ears 41 being received in the cavities 25. When the squeezing force is removed, the valve body 13 returns to its original annular configuration, leaving only the desired minimal clearance between the flat wall surfaces 23 of the valve body and the straight lateral edge surfaces 39 of the leaflets, in which positions the leaflets are slidably-pivotally mounted for travel between the open and closed positions. If employed, the metal stabilizing ring can be appropriately installed, as by snapping into place or by shrink-fitting, in the exterior circumferential groove 29 following the installation of the leaflets; however, it may be preferred to install such a metal stabilizing ring before installing the leaflets. Pyrocarbon is the preferred material of valve body construction, and compressive force applied to a pyrocarbon structure by such a metal ring can improve the structural properties of a pyrocarbon valve body. Such a metal ring may be chosen to have sufficient resiliency to return to its perfectly annular shape following removal of such a squeezing force.

When the heart valve is operatively installed in a patient, the two leaflets 15, in the open position, assume an equilibrium position with respect to the high flow of blood in the downstream direction in the valve body, which may be an orientation in which they are substantially parallel to the centerline plane, thus providing very low obstruction to the downstream flow of blood. This feature in combination with the entrance section of the valve body being essentially a section of the surface of torus having a particular radius of curvature in a valve body of relatively long axial length results in the achievement of smooth nonturbulent flow and the absence of stasis. Overall the valve 11 has a very low pressure drop for a passageway of a given diameter.

When reverse flow of blood upstream through the valve begins, the leaflets 15 translate upstream, with the ears 41 traveling upward in the upper lobes 57 of the recesses, which causes immediate camming engagement instigating the pivoting of the leaflets toward the closed position. As the pivoting of the leaflets proceeds, the force of the backflowing bloodstream against the outflow surface 33 of each leaflet becomes significant and begins to swing the leaflets at a greater velocity. As previously mentioned, the final movement is one of essentially only rotation, and the fully-closed position is achieved when the straight mating edges 37 of the two leaflets meet and the arcuate edge surfaces 35 of the leaflets abut against the cylindrical interior wall surface 17 of the valve body.

Because of manufacturing tolerances, it should be understood that it is simply not feasible to even try to perfectly match the curvature and shape of the arcuate edge surface 35 of the leaflet, which is a rectilinear surface, with the generally circular cylindrical interior wall surface 17 of the valve body, to try to obtain complete contact throughout the entire arcuate length, which might amount to about 110° to about 120° of arc. It should be understood that the need to provide for normal manufacturing tolerances and the need to avoid the danger of binding simply militate against any attempt to create a precise match in a commercial heart valve. Heretofore, bileaflet heart valves of this general type, wherein the rectilinear arcuate edges of the leaflets seat against the interior generally cylindrical surface of the valve body, were manufactured so that contact would occur at a single location adjacent the central tip or midpoint of the leaflet. As a result of manufacturing tolerances, such commercial valves have been designed so that the leaflets abut the interior wall at a single location within a few degrees of the centerline of the leaflet, and such leaflets are sized so that there is a gap less than some predetermined maximum size for the remainder of the periphery of the leaflet, including the regions along both lateral edges. The present invention deviates from this traditional valve design, creating a construction wherein there is at least a minimum gap at the very center tip of the leaflet.

Although the interior surface of the valve body is described as being of generally circular cylindrical construction, by generally circular is meant that the cross-sectional shape might be elliptical, oval or even hyperbolic; however, the two arcuate sections of the interior surface 17, which flank the two flat sidewall sections 23, preferably have a circular cross-section. Although these wall sections are preferably of regular circular cross-section, with the irregularities being formed in the arcuate edge 35 of each of the leaflets, a reversal of parts could be used to achieve the same result by machining the valve body 13 so as to have a pair of shallow ridges formed in the sidewall at the desired locations, which ridges would extend in an upstream-downstream direction parallel to the centerline of the valve body. However, any change in shape from entirely circular cross-section for the interior wall 17 in these two arcuate regions would result in some reduction in the cross-sectional area of the valve body passageway, and because high flow through the valve in the open position is considered to be a very important feature, a true circular cross-section is preferred for the interior wall surfaces.

The arcuate edge surface 35 of the leaflet is of course formed with a shape that is complementary to the particular generally circular cylindrical shape of the interior wall surface, so that the edge lies in juxtaposition with the interior surface in the closed position and so that a controlled gap is provided along the major length of the arcuate edge where there is no contact. The attitude or orientation of the leaflets 15 in the closed position determines the force vectors at the time of closing contact, and these vectors may have a substantial effect upon cavitation and noise which can occur at the instant of closing. As previously indicated, the angle between the centerline of the valve body and the outflow surface 33 of the leaflet in the fully closed position, which is referred to as the downstream angle, is marked in FIG. 2 with the reference letter alpha ($\alpha$). In most bileaflet valves, this angle $\alpha$ is between about 45° and about 70°. In the illustrated embodiment, this angle is about 50°, and whenever this angle is about 55° or less, it is particularly important that the potential for cavitation and noise at the instant of closing should be taken into consideration. It has been found that by creating two spaced apart locations of contact, rather than having contact occur at or very near the central tip or midpoint of the leaflet, cavitation can be minimized and any sound occurring at the instant of closure is greatly attenuated.

As previously mentioned, the ears 41 which extend laterally from each leaflet generally define the axis about which pivoting occurs (which is marked PA in FIG. 6), and the point on the arcuate edge of the leaflet which lies furthest from this axis is referred to as the midpoint or the central tip 71. A line extending from the tip 71 perpendicular to the pivot axis is considered to be the centerline of the leaflet and is marked with the reference CL in FIG. 5. As can be seen from this figure, the leaflet 15 is symmetrical about this centerline. The arcuate edge of the leaflet 15 is circular except for the irregularities at two locations, and the radius of curvature of the circular arcuate edge 35 is just slightly less than the radius of curvature of the interior wall 17 of the valve body.

Figure 7:
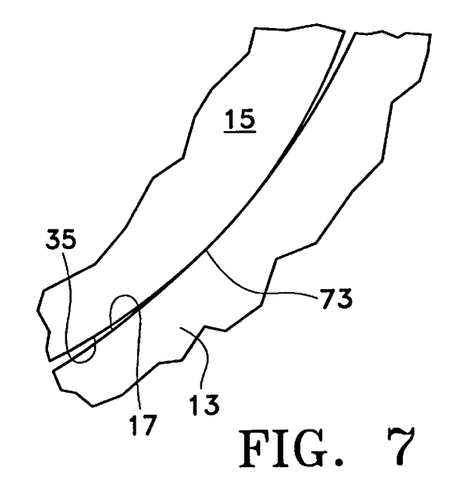
FIG. 7 is a fragmentary view of a portion of FIG. 6 greatly enlarged in size.

A pair of spaced apart bulges or protrusions 73, which are strategically placed on opposite sides of the centerline so as to flank the centerline, constitute the irregularities. The protrusions 73 constitute shallow bumps which extend radially outward from the remainder of the arcuate circular edge and thus are located further radially from the center of the generally semicircular leaflet. Generally, the height of these protrusions 73 (as perhaps best seen in exaggerated view FIG. 7) will be between about 0.001 inch and 0.005 inch.

The locations of the protrusions 73 are arranged so as to flank the centerline of the leaflet and so that each is spaced between about 20° and about 60° therefrom. Preferably, the spacing of these protrusions 73 is such that the points of contact between the leaflet edge and the valve body interior wall surface 17 lie at locations between about 30° and about 55° from the centerline so that there is no contact between the arcuate edge and the valve body interior wall for at least about 30° of arc on each side of the centerline, or at least 60° total at this location. Most preferably, the protrusions are positioned approximately as shown in FIGS. 5 and 6, so that the points of contact are each spaced about 45° from the centerline.

As previously indicated, the arcuate edge 35 of the leaflet is rectilinear, as is the interior wall surface 17 of the valve body. Accordingly, the edge of the leaflet will normally abut the interior wall surface along a line of contact extending in the upstream/downstream direction. However, there may be contact along short arcuate segments, i.e. segments of about 5° to about 10° of arc. Preferably, the line of contact or the short arc of contact will be located in the region between about 40° and about 50° arc from the central tip 71.

Figure 8:
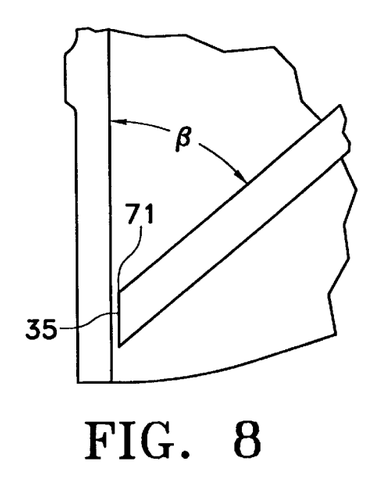
FIG. 8 is a fragmentary view of a portion of FIG. 2 greatly enlarged in size.

It is considered that the location and the height of the protrusions should be such that there is at least a minimum gap between the valve body interior wall and the central tip 71, i.e. at the leaflet centerline (see FIG. 8), which is between about 0.001 inch and about 0.005 inch, and which is preferably at least about 0.002 inch and more preferably about 0.003 inch. This gap preferably gradually lessens as one moves in either direction along the arcuate edge from the central tip toward the protrusions 73 where contact occurs. Generally, the gap will be between about 0.0005 and about 0.004 inch. The gap similarly widens as one travels from the protrusion 73 toward the end of the arcuate edge at the flat lateral surface where the gap is preferably between about 0.001 inch and about 0.004 inch and is more preferably at least about 0.002 inch.

It can be understood that as the leaflet 15 travels from its fully open position to its closed position, while pivoting about the pivot axis PA defined by the laterally extending ears 41, the tangential velocity of the leaflet will be greatest at the point on the circumference that is farthest from the pivot axis, which distance is represented by $l_2$ in FIG. 6, and it will be gradually less at locations moving away from the central tip 71 in both directions, with the distance at the point of contact being marked $l_1$. The velocity is accordingly less by a factor equal to $l_1/l_2$. This is one factor that has an effect from the standpoint of whether cavitation will occur, with the greatest effect being present when contact occurs at the tip 71. The creation of two spaced apart points of contact facilitates the establishment of at least a minimum gap at the tip 71. This gap overcomes the potential occurrence of cavitation at the point of greatest danger which can result in erosion and/or hemolysis, i.e. localized vaporization can occur at about the instant of closure which is followed by an immediate localized high pressure drop causing such minute vapor bubbles to implode (quickly collapse inward) which can result in erosion of the pyrocarbon that can lead to leaflet or valve body failure through cracking or in the rupture of red blood cells in the vicinity.

Cavitation can result from squeezing a liquid, i.e. blood, between two surfaces that are rapidly converging; in such an instance, the force vectors perpendicular to the interior wall of the valve body become an important consideration in the extent that such squeezing occurs. There are two factors to be considered along with the terminal velocity of the leaflet at the point where contact occurs: one is the orientation of the leaflet to the wall in the closed position, i.e. the angle β in FIG. 2, and the other is the location arcuately along the edge. These two factors are the components which determine the attitude at which contact occurs and thus the force or velocity vector perpendicular to the interior wall. The component from the orientation is equal to cosine β times the velocity; the other component from the arcuate location results in a further reduction equal to cosine 45° (see FIG. 6). In comparison to the force vector at the tip 71 of the valve 11, the reduction of cosine 50° is cancelled out, so the relative difference is less at the point 73 (than at the tip) by a factor equal to cosine $45°·l_1/l_2$ which is truly significant in combatting cavitation. Thus, the novel arrangement where the two leaflets in such a bileaflet valve each contact the interior wall of the valve body at points which are spaced apart at least about 40 angular degrees, preferably at least about 60 angular degrees and most preferably by about 90 angular degrees, not only provides an extremely quiet valve operation but avoids potential cavitation.

Although the invention has been described in terms of the preferred embodiments which constitute the best mode presently known to the inventors for carrying out the invention, it should be understood that various changes and modifications as would be obvious to one having the ordinary skill in this art may be made without deviating from the scope of the invention which is defined by the claims appended hereto. More particularly, although the valve body and the leaflet are preferably made from pyrocarbon-coated graphite structures, they could be made entirely of pyrocarbon or could be made of other suitable biocompatible materials. Although the arcuate interior walls of the valve body are preferably of true circular cross-section so as to maximize the flow passageway through the valve with the leaflets in the open position, protrusions in the shape of shallow ridges could be provided at desired locations in the walls that would engage the regular edges of the leaflets; however, any such alternative arrangement should be such so that engagement occurs generally as line contact between the rectilinear edge of the leaflet and the wall of the valve body. Although flat leaflets are illustrated, the leaflets may have a simple or even complex curvature, if desired, generally as illustrated in various of the U.S. patents mentioned hereinbefore.

Although the invention is illustrated in the form of a bileaflet valve, where it is considered to have its primary value inasmuch as these are presently the valves of choice throughout the world, it could also be incorporated in a single occluder valve having a defined pivot axis, such as those shown in the '937 patent to Klawitter and the '111 patent to Bokros et al., or in a trileaflet valve such as that shown in U.S. Pat. No. 5,628,791 (May 13, 1997).

Particular features of the invention are set forth in the claims which follow.

What is claimed is:

1. A prosthetic heart valve which comprises
   a tubular valve body having an interior wall surface of generally circular cross-section which has a pair of opposed flat sidewall sections,
   said sidewall sections being parallel to each other and located so as to be diametrically opposed,
   two leaflets mounted within said valve body on pivot means so as to alternately open to permit blood flow downstream through said valve body and close to prevent blood flow therethrough, said leaflets pivoting on axes that are parallel to each other and perpendicular to said flat sidewall sections, said valve body interior wall surface in each of the two opposite regions between said flat sidewall sections being uninterrupted rectilinear surface, said leaflets each having a flat edge, which interengages with the flat edge of said other leaflet in the closed position, and a major arcuate edge, which is formed with a central tip of greatest extension and terminates at each end in a flat lateral edge, said arcuate leaflet edge having a surface which substantially rectilinear, being composed of lines which are substantially parallel to said flat sidewall sections in the closed position, said arcuate edge and said pair of lateral edges lying in juxtaposition with said generally circular cross-section interior wall of said valve body and said flat sidewall sections, respectively, in the closed position, and said arcuate edge of each leaflet and said interior generally circular cross-section rectilinear wall surface being shaped so that (a) said arcuate edge is spaced from said rectilinear interior wall surface at said central tip, and (b) there is generally line contact between each said arcuate edge and said rectilinear interior wall surface at two spaced apart locations at distances between about 20° and about 60° of arc in opposite directions from said central tip.

2. The prosthetic valve according to claim 1 wherein said valve leaflets have inflow and outflow surfaces which are flat.

3. The prosthetic valve according to claim 2 wherein the angle in a downstream direction between the centerline of the valve body and said flat outflow surface of said leaflet in the closed position is between about 45° and about 70°.

4. The prosthetic valve according to claim 2 wherein the angle in a downstream direction between the centerline of the valve body and said flat outflow surface of said leaflet in the closed position is about 55° or less.

5. The prosthetic valve according to claim 1 wherein said arcuate edge of each leaflet is irregular in outline having two protrusions which extend radially outward from a generally semicircular perimeter.

6. The prosthetic valve according to claim 5 wherein said valve body interior wall surface includes two sections of a cylindrical surface of circular or elliptical cross-section, which sections are separated by said opposed flat sidewall sections.

7. The prosthetic valve according to claim 1 wherein said central tip of said arcuate edge of said leaflet is spaced between about 0.001 inch and about 0.005 inch from said interior surface of said valve body.

8. The prosthetic valve according to claim 1 wherein said central tip of said arcuate edge of said leaflet is spaced at least about 0.002 inch from said interior surface of said valve body.

9. The prosthetic valve according to claim 1 wherein there is no contact between said arcuate edge of each leaflet and said valve body wall for at least about 30° of arc on each side of said central tip.

10. The prosthetic valve according to claim 1 wherein said points of contact lie at a location between about 30° and about 55° from said central tip.

11. The prosthetic valve according to claim 10 wherein there is a gap between the remainder of said arcuate edge and said interior wall surface of between 0.0005 inch and about 0.004 inch in the closed position.

12. The prosthetic valve according to claim 11 wherein said interior surface of said valve body has a generally circular cylindrical surface and said arcuate edge is irregular in shape having two locations each protrude radially outward from the remainder of said arcuate edge.

13. The prosthetic valve according to claim 1 wherein said two points of generally line contact between said arcuate edges and said valve body interior surface comprise contact along a line or along short segments of about 5° of arc or less at locations between about 40° and about 50° of arc from said central tip.

14. The prosthetic valve according to claim 1 wherein said pivot means includes means laterally extending from opposite edges of each leaflet and recesses within said flat sidewall sections of said valve body which receive said laterally extending means.

15. A prosthetic heart valve which comprises a tubular valve body having an interior wall surface of generally circular cylindrical cross-section, at least one occluder mounted within said valve body so as to alternately open to permit blood flow downstream through said valve body and to pivot closed to prevent blood flow therethrough, said occluder having a major arcuate edge a central tip portion thereof lies at a point of greatest extension from an axis on which said pivoting to said closed position occurs, said arcuate edge lying in juxtaposition with said generally circular cylindrical cross-section interior wall of said valve body in said closed position, and said arcuate edge of said occluder being rectilinear and said interior generally circular cylindrical wall surface lying in juxtaposition with said arcuate edge being an uninterrupted rectilinear surface, with said arcuate edge and said rectilinear wall surface being shaped so that (a) said arcuate edge is spaced from said interior wall surface at said central tip portion, and (b) there is generally line contact between said arcuate edge and said interior wall surface at two spaced apart locations each between about 20° and about 60° of arc in opposite directions from said central tip portion.

16. The prosthetic valve according to claim 15 wherein the portion of said interior wall surface in juxtaposition with said arcuate edge is a section of a surface of a cylinder of circular or elliptical cross-section and wherein said arcuate edge is circular except for two radial protrusions which are spaced apart by at least about 60° of arc.

17. The prosthetic valve according to claim 15 wherein said central tip portion of said arcuate edge of said occluder is spaced at least about 0.002 inch from said interior wall surface of said valve body and wherein said two spaced apart locations of contact between said arcuate edge and said valve body interior wall surface comprise contact along a line or along short segments of about 5° of arc or less at locations between about 40° and about 50° of arc from said central tip portion.

18. A bileaflet prosthetic heart valve which comprises a generally annular valve body having an interior wall of generally circular cross-section that defines a blood flow passageway therethrough and which includes an entrance region and a main downstream region, said main region being an uninterrupted rectilinear surface except for a pair of diametrically opposed flat sidewall sections, and two leaflets mounted in association with said valve body to pivot about eccentric axes so as to alternately open to permit blood flow downstream through said valve body and close to prevent blood flow therethrough in an upstream direction, said valve body having recesses in said flat sidewall sections for receiving ears extending in opposite directions from said leaflets to define said pivot axes, each said leaflet having a major arcuate edge which is rectilinear and is proportioned to lie in juxtaposition with said rectilinear wall surface of said valve body in said closed position to block blood flow in the upstream direction through said passageway, and said rectilinear major arcuate edge of each said leaflet and said rectilinear generally circular wall being proportioned and shaped so that a tip portion of said leaflet major arcuate edge lying farthest from said pivot axis is spaced from said wall as a result of which, contact between said major arcuate edge and said valve body that determines said closed position of said occluder occurs at two spaced apart locations which are lines of contact that are offset in opposite directions from said tip portion, with each of said lines of contact being located at between about 40° and about 50° of arc from the center of said tip portion.

* * * * *